US010548770B2

(12) United States Patent
Rathjen

(10) Patent No.: US 10,548,770 B2
(45) Date of Patent: Feb. 4, 2020

(54) OPHTHALMOLOGICAL APPARATUS FOR THE REFRACTIVE CORRECTION OF AN EYE

(75) Inventor: Christian Rathjen, Bremen (DE)

(73) Assignee: SIE AG SURGICAL INSTRUMENT ENGINEERING (CH)

(*) Notice: Subject to any disclaimer, the term of this patent is extended or adjusted under 35 U.S.C. 154(b) by 2451 days.

(21) Appl. No.: 11/898,031

(22) Filed: Sep. 7, 2007

(65) Prior Publication Data

US 2008/0077121 A1 Mar. 27, 2008

(30) Foreign Application Priority Data

Sep. 7, 2006 (EP) .................................... 06405385

(51) Int. Cl.
*A61F 9/008* (2006.01)

(52) U.S. Cl.
CPC .......... *A61F 9/008* (2013.01); *A61F 9/00827* (2013.01); *A61F 9/00838* (2013.01); *A61F 2009/00897* (2013.01)

(58) Field of Classification Search
CPC .. A61F 9/008; A61F 9/00827; A61F 9/00838; A61F 2009/00846; A61F 2009/00848; A61F 2009/0087; A61F 2009/00872; A61F 2009/0088; A61F 2009/00897
USPC .................................................. 606/5, 10–13
See application file for complete search history.

(56) References Cited

U.S. PATENT DOCUMENTS

| | | | | |
|---|---|---|---|---|
| 3,948,248 A | * | 4/1976 | Zuckerman | A61B 3/165 600/463 |
| 4,907,586 A | * | 3/1990 | Bille et al. | 606/5 |
| 5,061,342 A | * | 10/1991 | Jones | A61F 9/008 606/10 |

(Continued)

FOREIGN PATENT DOCUMENTS

| | | |
|---|---|---|
| EP | 1 486 185 A1 | 12/2004 |
| EP | 1 731 120 A1 | 12/2006 |

OTHER PUBLICATIONS

Rozema et al., "Clinical comparison of 6 aberrometers. Part 1: Technical specifications," *J. Cataract Refract. Surg.*, vol. 31, Jun. 2005, p. 1114-1127.

*Primary Examiner* — Tammie K Marlen
(74) *Attorney, Agent, or Firm* — Ostrolenk Faber LLP

(57) ABSTRACT

An opthalmological apparatus for the refractive correction of an eye comprises a light projector for projecting laser pulses on to a focal point in the interior of the eye in order to break down eye tissue. The apparatus further comprises a positioning module for positioning the focal point (F) at different starting points, and a scanning module for moving the focal point (F) starting from, in each case, one of the starting points in accordance with a scanning pattern for a treatment subarea (a), the scanning pattern and the starting points being defined such that in a number of treatment subareas (a) separated from one another by tissue bridges, the eye tissue is broken down. Through the formation of a multiplicity of separate, disconnected treatment subareas (a) with broken down eye tissue, it is possible not simply to (Continued)

flatten off the curvature of the cornea (21) in order to correct a myopia but to change the curvature of the cornea (21) at virtually any desired locations and, in particular, also to change it asymmetrically for a refractive correction.

15 Claims, 4 Drawing Sheets

(56) References Cited

U.S. PATENT DOCUMENTS

| | | | | |
|---|---|---|---|---|
| 5,257,132 | A * | 10/1993 | Ceglio | G02B 5/188 359/565 |
| 5,993,438 | A * | 11/1999 | Juhasz | A61F 9/008 606/10 |
| 6,099,522 | A * | 8/2000 | Knopp et al. | 606/10 |
| 6,296,867 | B1 * | 10/2001 | Peyman | 351/160 R |
| 6,325,792 | B1 | 12/2001 | Swinger et al. | |
| 6,551,307 | B2 * | 4/2003 | Peyman | 606/5 |
| 6,726,679 | B1 * | 4/2004 | Dick | A61F 9/008 128/898 |
| 2003/0038921 | A1 | 2/2003 | Neal et al. | |
| 2004/0199149 | A1 | 10/2004 | Myers et al. | |
| 2004/0243111 | A1 | 12/2004 | Bendett et al. | |
| 2004/0243112 | A1 | 12/2004 | Bendett et al. | |
| 2004/0254568 | A1 | 12/2004 | Rathjen | |
| 2008/0001320 | A1 * | 1/2008 | Knox | A61F 9/008 264/1.37 |
| 2008/0039825 | A1 * | 2/2008 | Lai | A61F 9/00829 606/5 |

* cited by examiner

OPHTHALMOLOGICAL APPARATUS FOR THE REFRACTIVE CORRECTION OF AN EYE

TECHNICAL FIELD

The present invention relates to an opthalmological apparatus for the refractive correction of an eye. The invention relates, in particular, to an opthalmological apparatus for the refractive correction of an eye by means of projection of laser pulses on to a focal point in the interior of the eye for breaking down eye tissue.

PRIOR ART

Ametropias such as myopia, hyperopia or astigmatism can nowadays be permanently corrected by refractive surgical treatment. Refractive surgical treatments are surgical interventions on the eye which change the optical refractive power of the eye with the aim of approximating the latter to a desired value as well as possible. Transparent materials at the focus can be treated by nonlinear absorption and subsequent interaction (for example, photodisruption) by means of femto laser systems which have pulse widths of typically 10 fs to 1000 fs (1 fs=$10^{-15}$ s). In particular, in practice, operative incisions are made in the cornea by breaking down tissue with the aid of femto laser pulses.

Patent specification U.S. Pat. No. 5,993,438 describes a method for the refractive keratectomy in the cornea by means of pulsed laser beams. In accordance with U.S. Pat. No. 5,993,438, breaking down tissue in the interior of the cornea produces a dome-shaped cavity around the optical axis which is suitably varied upon breaking down the cornea curvature. The continuous cavity is formed by a number of directly superimposed ablation layers which are arranged centrosymmetrically around the optical axis of the eye. Each of the ablation layers is produced centrosymmetrically around the optical axis by, for example, laser pulses lined up spirally one after another. The ablation layers respectively exhibit a decreasing diameter with decreasing distance from the corneal surface. According to U.S. Pat. No. 5,993,438, the distance between the focal diameters of consecutive laser pulses is preferably one to two times the radius of a blister produced by one of the laser pulses at the focal point. The eye tissue is respectively broken down in an ablation layer over a thickness of approximately 10 µm. The superimposed ablation layers are respectively produced in a directly juxtaposed fashion such that the dome-shaped cavity is formed continuously without remaining tissue bridges. The method according to U.S. Pat. No. 5,993,438 is certainly suitable for treating myopia, but the dome-shaped cavity is not suitable for correcting hyperopia, astigmatism or higher-order aberrations.

Patent specification U.S. Pat. No. 6,325,792 describes an apparatus for eye surgery by means of femtosecond lasers in which the focal point can be positioned in two dimensions at any desired location. The most varied forms of incision can be produced in the eye tissue by means of a scanner, in particular a number of mutually separated radial incisions can be applied on the cornea.

Patent application US 2004/0199149 describes an apparatus for laser based eye surgery which produces lens corrections on the basis of a multiplicity of microspheres arranged next to and above one another, the microspheres respectively being formed by a pulse in a "punctiform" fashion at a focal point. US 2004/0199149 describes in particular the accumulation of a number of separate punctiform microspheres to form a cluster with a higher-order annular or disc structure.

SUMMARY OF THE INVENTION

It is an object of the present invention to propose a novel opthalmological apparatus for the refractive correction of an eye by means of laser pulses which, in particular, is not limited to the correction of short sightedness.

In accordance with the present invention, these aims are achieved in particular by means of the elements of the independent claims. Further advantageous embodiments emerge, furthermore, from the dependent claims and the description.

The above-named aims are achieved by the present invention by virtue of the fact that, in particular, the opthalmological apparatus, which comprises a light projector for projecting laser pulses on to a focal point in the interior of the eye to break down eye tissue, comprises in addition a positioning module and a scanning module. The positioning module is configured to position the focal point at different starting points. The scanning module is configured to move the focal point starting from, in each case, one of the starting points in accordance with a scanning pattern for a treatment subarea, the scanning pattern and the starting points being defined such that in a number of treatment subareas separated from one another by tissue bridges, the eye tissue is broken down. The scanning pattern defines, for example, a treatment subarea whose shape is selected as rectangular, round, elliptical, that of a star or that of a spiral shape or that of a shape similar to a Lissajou figure. For deflecting the laser pulses, the scanning module comprises, for example, a galvanoscanner, a resonant mirror scanner, an acoustic optical modulator, a polygonal scanner and/or a microelectromechanical scanner. The positioning module comprises movement drivers for mechanically displacing at least parts of the light projector, and/or a galvanoscanner for deflecting the laser pulses. The light projector preferably has a numerical aperture above 0.3. The opthalmological apparatus comprises, for example, a control module which is configured to control the positioning module and the scanning module such that the positioning module positions the focal point at different starting points, and that the scanning module moves the focal point in accordance with the scanning pattern, starting from one of the starting points in each case such that the eye tissue is broken down in a number of treatment subareas separated from one another by tissue bridges. Through the formation of a multiplicity of separate, disconnected treatment subareas with broken down eye tissue, it is possible not simply, as in the prior art, to flatten off the curvature of the cornea centrosymmetrically in order to correct a myopia, but to change the curvature of the cornea at virtually any desired locations and, in particular, also to change it asymmetrically for a refractive correction. For example it is possible by suitable selection of the starting points to arrange a number of the treatment subareas in an annular cluster in the (intrastromal) corneal tissue such that a hyperopia can be corrected. The corneal curvature can be suitably varied in order to correct astigmatism and higher-order aberrations by means of a different distribution of the treatment subareas in the cornea, both in depth and in distance from the optical axis of the eye and/or by means of a multilayer arrangement of the treatment subareas in the corneal tissue. Alongside the treatment and correction of the cornea, it is also additionally possible to use the opthalmological apparatus in the same way to treat the tissue of the lens, in particular to improve the elasticity of the lens in the case of hyperopia with age.

In a preferred embodiment, the positioning module is configured to position the focal point respectively at starting points on a first treatment surface, and the scanning module is configured to move the focal point on this first treatment surface. The opthalmological apparatus additionally comprises a depth positioning module for displacing the focal point along a projection axis of the light projector on to a second, for example parallel, treatment surface equidistant from the first treatment surface such that the focal point can be positioned on the second treatment surface at different starting points and can be moved in accordance with the scanning pattern starting from one of the starting points in each case. The depth positioning of the focal point can be used to set a number of focal surfaces, for example, focal planes, which respectively form a treatment surface, for example, treatment plane, on which the starting points are respectively defined and the eye tissue is broken down in treatment subareas. The depth positioning of the focal point therefore facilitates a multilayer treatment of the eye tissue with in each case a multiplicity of separate, discontinuous subareas in which the eye tissue is broken down. In this case, the distance between individual focal surfaces or treatment surfaces is preferably determined such that a tissue bridge respectively remains in existence in the case of superimposed treatment subareas of neighboring treatment surfaces. To this end, the control module is further preferably configured to control the depth positioning module such that a minimum distance between the treatment surfaces is observed upon displacement of the focal point, the minimum distance being defined such that treatment subareas superimposed on equidistant (parallel) treatment surfaces are separated from one another by tissue bridges. The aim and advantage of the tissue bridges consists in that defined ablation layer thicknesses can be produced. Specifically, it has emerged that internal gas pressures arising during laser treatment produce a deformation of the tissue which greatly impairs precision in the layerwise ablation of large continuous layers, as described in the prior art.

In one embodiment, the control module is configured to determine in accordance with a desired refractive correction of the eye the number of the treatment subareas and the starting points for the spatial distribution of the treatment subareas on a number of treatment surfaces in the interior of the eye. The control module determines the spatial distribution of the treatment subareas, for example, on the basis of a model of the eye tissue to be treated, for example, a corneal model, given a prescribed size and shape of the treatment subareas and given prescribed vertical and horizontal minimum spacings of individual treatment subareas.

In one embodiment, the control module is further configured to select different scanning patterns for treatment subareas of different size.

In a preferred embodiment, the apparatus comprises one wavefront detector for determining a wavefront profile of a light bundle reflected by the eye. The control module is additionally configured to define the starting points on the basis of the determined wavefront profile. That is to say, the control module is configured to define the spatial distribution of the treatment subareas on the basis of the wavefront profile determined. It is thereby possible to measure the refractive correction achieved during treatment and, on the basis thereof, to determine the positioning of further treatment subareas to the extent required.

The scanning module is preferably configured to position consecutive laser pulses such that their focal diameters partially overlap. Their focal diameters preferably overlap at least as far as half their diameter. Owing to the overlapping of the focal diameters, it is possible to use laser pulses of low pulse energy for the breakdown of tissue, as a result of which only slight mechanical stresses are induced by gas and cavitation bubbles in the residual tissue and this assists in the formation of uniformly thin ablation areas and promotes a defined breakdown of the treatment subareas. Very regular ablation volumes can be produced in conjunction with low height and small aspect ratio (approximation to a sphere) particularly together with the use of high numerical apertures, for example>0.3, in particular >0.4, and the low requisite pulse energies associated therewith. It is even possible to produce incisions with little gas or none in conjunction with a high numerical aperture and pulses of very short duration and low energy. Overheating such as mentioned in the prior art does not occur in this case even given large overlaps of individual laser pulses.

The scanning module is preferably configured to move the focal point much more quickly than the speed of movement of a human eye when changing direction of view. When the eye is not mechanically fixed during treatment and moves, although the size of the treatment subarea defined by the scanning pattern can then be slightly varied by the eye movement, the scanning module still moves the focal point quickly enough to prevent tissue bridges remaining in the treatment subarea on the basis of the eye movements. In addition, the apparatus comprises an eye tracking module for determining eye movements, and is configured to drive the positioning module for an appropriate positioning compensation on the basis of the determined eye movements. Since the positioning module positions the focal point with a substantially smaller frequency than the scanning module, eye movements also exert correspondingly less influence on the positioning of the focal point at the starting points. The influence of the eye movement can respectively be compensated during the positioning of the focal point at a new starting point by the determination of the eye movements, for example, on the basis of iris or vein patterns (on the sclera or the retina). The high deflection rate of the scanning module for the production of cavities corresponding to the scanning module, and the compensation of eye movements in the positioning of the starting points enable the refractive correction of the eye without the need to fix the eye therefore at the light projector. Movement artefacts are averaged out of the ablation result by the high number of treatment subareas, for example, a hundred. The production of the multiplicity of separate cavities at a high deflection rate, and the compensation of the eye movements in the positioning of the cavities, therefore enable the refractive correction of the eye by means of laser pulses without the need for the eye and/or the patient to be connected or to be fixed mechanically to the laser system in some way or other.

The scanning pattern preferably defines a treatment subarea whose diameter is smaller than the thickness of the cornea. When the dimensions of the treatment subarea with broken down eye tissue are smaller than the thickness of the cornea, the loss in thickness visible at the corneal surface is smaller than would correspond to the height of the broken down eye tissue, particularly when the treatment subarea with the broken down eye tissue is remote from the corneal surface (for example, more than half a focal diameter). This effect (the restricted thickness reduction at the corneal surface) can be influenced via the lateral extent (diameter) and the depth positioning of a treatment subarea. Thus, treatment subareas whose diameter is smaller than the thickness of the cornea can be used to attain changes in refractive power which are smaller than the change in refractive power corresponding to the broken down height of the tissue. In accordance with a rule of thumb for LASIK (Laser-Assisted In Situ Keratomileusis), a corneal ablation of 12 μm for example, approximately corresponds to a dioptre. It is thereby possible by breaking down eye tissue in small treatment subareas remote from the corneal surface to undertake corrections of the refractive power which are finer than would be possible through an extended breakdown of tissue of the same height by means of the same laser pulses.

BRIEF DESCRIPTION OF THE DRAWINGS

A design of the present invention is described below with the aid of an example. The example of the design is illustrated by the following enclosed figures.

WAYS OF IMPLEMENTING THE INVENTION

Figure 1A:
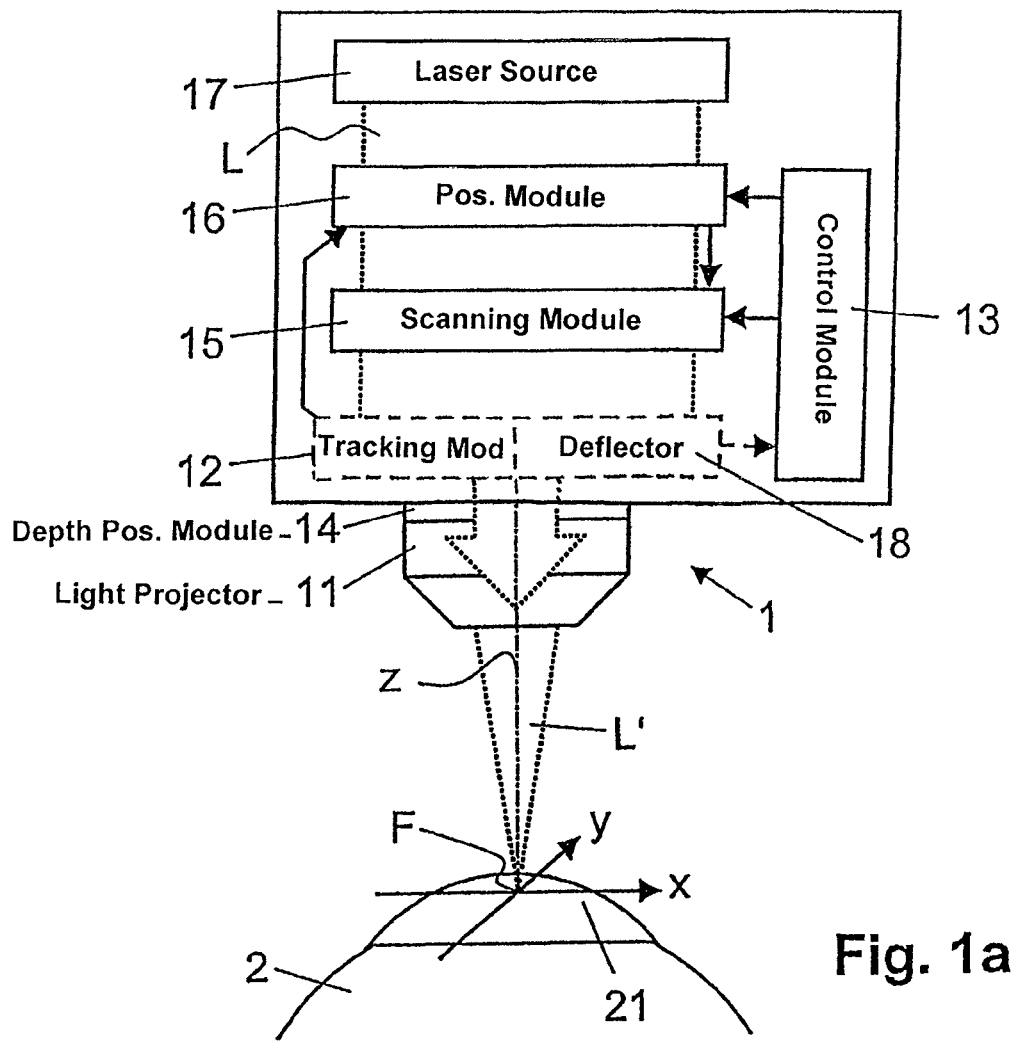
FIG. 1a shows a block diagram which represents diagrammatically an opthalmological apparatus used in treating an eye by means of a focused pulsed laser beam.

In FIG. 1a, the reference symbol 1 denotes an opthalmological apparatus or an opthalmological arrangement of apparatus having a laser source 17 and a light projection module 11, optically connected to the laser source 17, for the generation and focused projection of a pulsed laser beam L' for the punctiform breakdown of tissue at a focal point F (focus) in the interior of the eye tissue, for example, in the cornea 21. The laser source 17 comprises, in particular, a femtosecond laser for generating femtosecond laser pulses which have pulse widths of typically 10 fs to 1000 fs (1 fs=$10^{-15}$ s). The laser source 17 is arranged in a separate housing or in a common housing with the light projection module 11.

It may be adduced here for better understanding that FIG. 1a is a diagrammatic and simplified illustration of the opthalmological apparatus 1. For example, it is not reproduced precisely in FIG. 1a that the optical light projection module 11 has a high numerical aperture of at least 0.3 and preferably more than 0.4, that the opthalmological apparatus 1 optionally has a suction ring for fastening at the eye 2, or that the opthalmological apparatus 1 optionally comprises a contact body (for example an applanation body) for contact-based deformation (for example, for applanation) of the eye 2 during application of the opthalmological apparatus 1.

As is illustrated diagrammatically in FIG. 1a, the opthalmological apparatus 1 comprises a positioning module 16 and a scanning module 15 which are arranged in the diagrammatically illustrated beam path L between the laser source 17 and exit of the light projection module 11. The person skilled in the art will understand that the positioning module 16 and the scanning module 15 can also be arranged in reverse order than that illustrated in FIG. 1a. The positioning module 16 and the scanning module 15 are cascaded scanner modules which position or move the focal point F. The positioning module 16 is a substantially slower scanner module than the scanning module 15.

The positioning module 16 is configured to position the focal point F at defined starting points. The positioning module 16 comprises, for example, movement drivers for mechanically displacing the light projector 11 or parts of the light projector 11, for example, movement drivers for the lateral displacement of lenses. The movement drivers comprise, for example, a drive element for a feed direction x and a drive element for a scanning direction y, perpendicular to the feed direction x (see FIG. 1b), for example piezo motors. In one embodiment the positioning module 16 comprises a galvanoscanner for deflecting the laser pulses in the feed direction x and/or in the scanning direction y. The coordinates of the starting points are fed to the positioning module 16, preferably by the control module 13, for example, point for point or as a data file with (for example a sequence of) a number of starting points for storage in the positioning module 16.

Figure 1B:
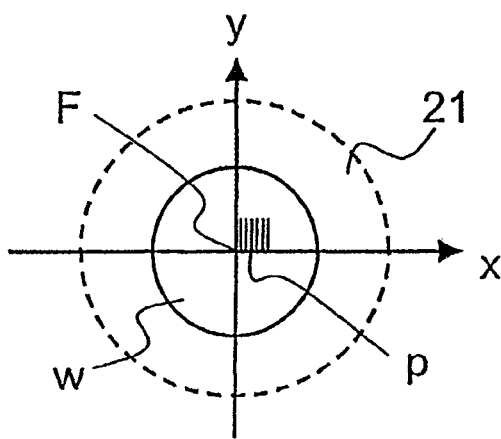
FIG. 1b shows a top view of a treatment surface treated by the opthalmological apparatus in accordance with a scanning pattern.
Figure 4:
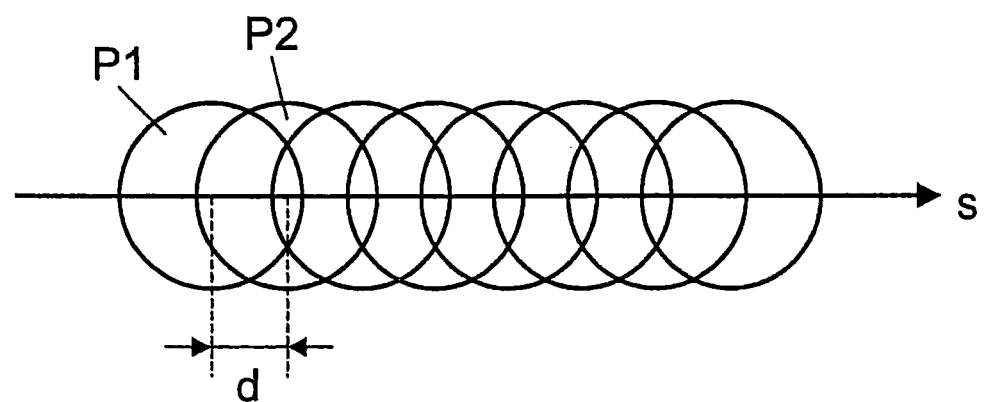
FIG. 4 shows in top view the overlap of the focal diameters of a number of consecutive laser pulses.

The scanning module 15 is configured to move the focal point F in accordance with a defined scanning pattern p starting from the current starting point (see FIG. 1b). In order to move the laser pulses in accordance with the prescribed scanning pattern p, the scanning module 15 comprises deflecting elements, for example, a galvanoscanner, a resonant mirror scanner, an acoustic optical modulator (AOM), a polygonal scanner or a microelectromechanical scanner (MEM). In order to position in a feed direction x which is much slower by comparison with the scanning direction y, in one variant the scanning module 15 comprises movement drivers for mechanically displacing the light projector 11 or parts of the light projector 11, that is to say the movement in the slower feed direction x of the scanning pattern p can be executed, for example, by the positioning module 16. The scanning module 15 is set up either permanently for a specific scanning pattern p, or for a number of selectable scanning patterns p. The scanning pattern p defines, for example, a treatment subarea a which is, for example, of rectangular, round, elliptical, star or spiral shape or that of a Lissajou figure, and specifies corresponding deflections of the laser pulses in the feed direction x and in the scanning direction y. For the purpose of refractive correction of the cornea 21, the scanning pattern p preferably defines a treatment subarea a whose diameter is smaller than the thickness of the cornea 21. The scanning module 15 preferably comprises control of the deflection elements for moving the focal point F in accordance with the scanning pattern p but the person skilled in the art will understand that the control module 13 can also perform the control. If appropriate, a scanning pattern p is selected by the control module 13, for example, by appropriate selection instructions or control sequences for the relevant selected pattern p. The scanning module 15 is additionally configured to deflect the laser pulses such that the focal diameters P1, P2 of consecutive laser pulses partially overlap. As illustrated in FIG. 4, the focal diameters P1, P2 of laser pulses which are consecutive in the scanning direction s preferably overlap by more than half their diameter, that is to say the distance d between the centres of the focal diameters P1, P2 is smaller than the radius of the focal diameters P1, P2. The scanning module 15 is configured to move the focal point F much more quickly than the human eye moves when changing directional view. In particular, the scanning module 15 is configured to deflect the laser pulses so quickly that the eye tissue is broken down in a treatment subarea a defined by the scanning pattern, without tissue bridges remaining therein, even when the eye 2 moves. The overall scanning pattern p for a treatment subarea is traversed by the scanning module 15 in 1 ms (millisecond), for example. When the scanning module 15 is set up, for example, to traverse a scanning pattern with 20 KHz in the feed direction x, it is possible in 1 ms to move 20 scanning lines in the scanning direction y, and given a focal diameter in the range, for example, of 5 μm to 20 μm the eye tissue is broken down in a treatment subarea a with a diameter in the range of approximately 100 μm to 400 μm (this value is reduced correspondingly given overlapping of the focal diameters P1, P2 in the feed direction x). Any possible eye movement in the x direction will stretch or compress this range slightly, a continuous incision always being ensured.

An opthalmological apparatus having a mechanical movement of the light projector and a superposition of an additional fine movement of the focal point F by means of optical microscans is described in EP 1 486 185, which is incorporated here by reference. In European Patent Application No. 05 405 376 (not yet published) there is a description of a scanner module for deflecting the pulsed light beam for the additional fine movement, as well as of an optical transmission system for transmitting the deflected femtosecond laser pulses from the scanner module to the light projector 11 and for superimposing the deflected femtosecond laser pulses on the movement of the light projector 11.

Figure 3A:
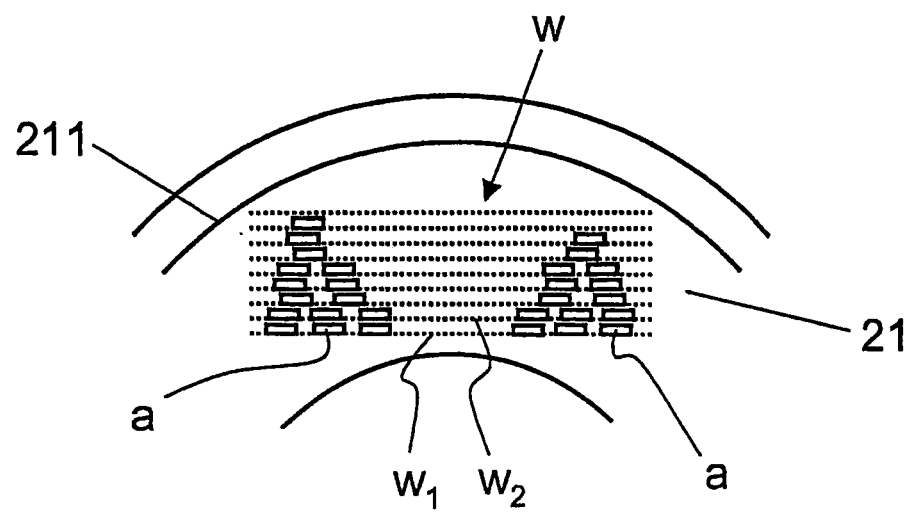
FIG. 3a shows a cross section through a segment of a cornea in which, for the purpose of refractive correction, eye tissue in a multiplicity of mutually separated treatment subareas is broken down.
Figure 3B:
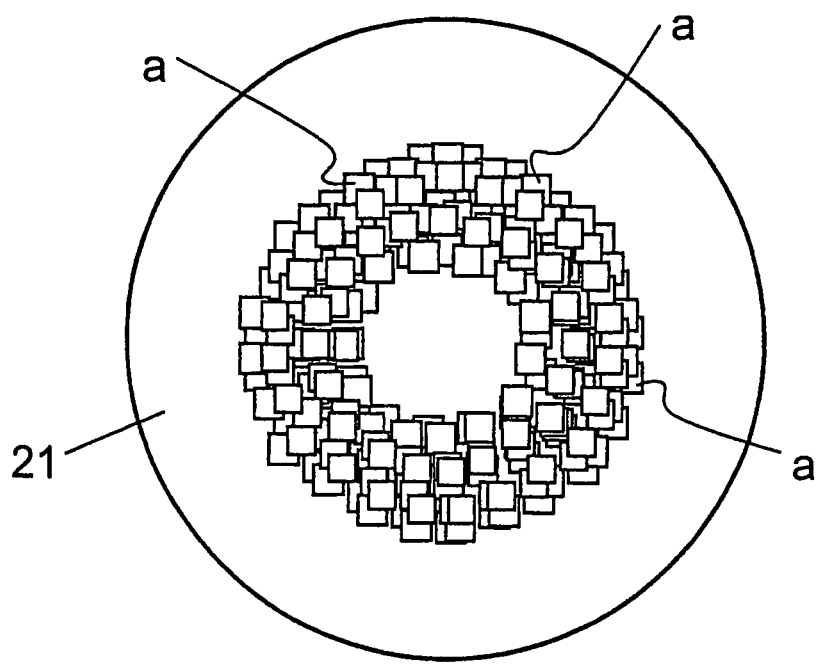
FIG. 3b shows a top view of a cornea in which, for the purpose of refractive correction, tissue is broken down in a multiplicity of treatment subareas which do not touch one another and are arranged next to one another in an annular cluster and superimposed.
Figure 3C:
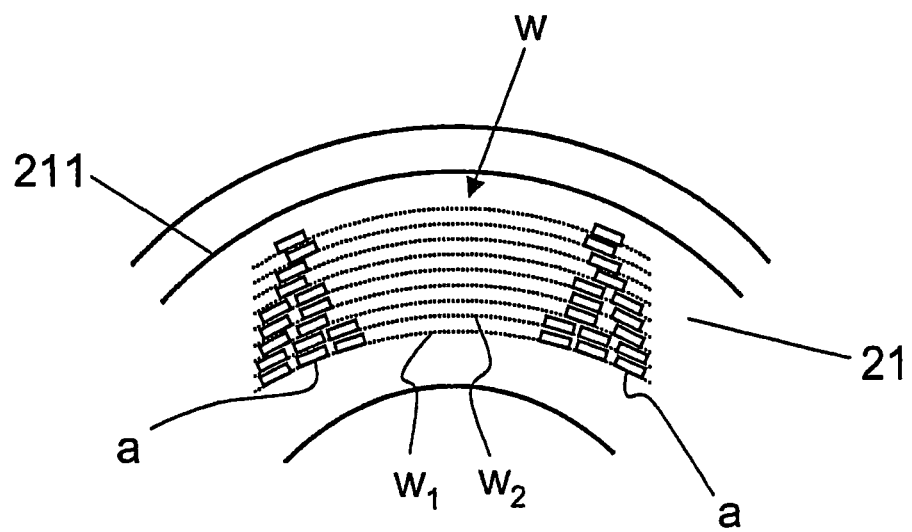
FIG. 3c shows a further cross section through the segment of the cornea in which the mutually separated treatment subareas are arranged in equidistant; curved treatment surfaces.

As illustrated diagrammatically in FIG. 1a, the opthalmological apparatus 1 additionally comprises a depth positioning module 14 for displacing the focal point F along a projection axis z of the light projector 11, for example, perpendicular to a treatment surface defined by the feed direction x and the scanning direction y, in particular a treatment plane w. In order to displace the focal point F the depth positioning module 14 preferably comprises a movable focussing lens and a drive element coupled thereto. In an alternative variant, the light projector 11 is moved mechanically to set the depth. As illustrated in the diagrammatic cross section of FIG. 3a, setting the depth of the focal point F defines focal planes or focal surfaces of different depth which serve as treatment planes or treatment surfaces w, $w_1$, $w_2$ on which the eye tissue, for example, the cornea 21, is respectively broken down in a number of mutually separated treatment subareas a defined by scanning patterns p. In addition to the flat treatment surfaces w, $w_1$, $w_2$ illustrated in FIG. 3a, the treatment surfaces w, $w_1$, $w_2$ can also, as illustrated in FIG. 3c, be given a curved (concave, convex) configuration by setting the depth of the focal point F under appropriate control or by using objectives with spherical image fields in the light projector 11. The breakdown of tissue produces in each of the treatment subareas a cavity which is separated by tissue bridges in each case from the other cavities, both on the same treatment surface w, $w_1$, $w_2$ and on neighboring superimposed treatment surfaces $w_1$, $w_2$. Preferably, the treatment subareas a are arranged remote from the corneal surface, preferably below the Bowman's membrane 211 of the cornea 21. FIG. 3b illustrates in plan view an example of a multiplicity of treatment subareas a which do not touch one another (for example, a hundred or more), which are arranged in an annular cluster next to one another and in a superimposed fashion, in order to form a multiplicity of mutually separated, disconnected cavities which are broken down and thereby suitably change the corneal curvature for a desired refractive correction of the cornea 21.

In a further embodiment the opthalmological apparatus 1 comprises a wavefront detector 18 for determining a wavefront profile of a light bundle reflected by the eye 2. The reflected light bundle is an additional reference light beam which is reflected by the fundus of the eye and is fed to the wavefront detector 18 by means of optical elements. The wavefront detector is, for example, designed as a Shack-Hartmann sensor, for example, according to US 2003/0038921, or as an Interferometer, for example, as a Shearing interferometer. Further possible embodiments of the wavefront detector are described in Jos. J. Rozena, Dirk E. M. Van Dyck, Marie-José Tassignon, "Clinical comparison of 6 aberrometers. Part 1: Technical specifications", J Cataract Refract. Surg., Volume 31, June 2005, pages 1114-1127. The wavefront detector 18 is connected to the control module 13 in order to feed back the specific wavefront profile. The control module 13 is configured to determine the refractive correction of the cornea 21 currently achieved by doing so on the basis of the wavefront profile determined, and to determine on this basis the spatial distribution of further treatment subareas a or the starting points for corresponding sampling patterns p, in order to achieve the desired refractive correction of the cornea 21. Depending on embodiment, the determination of the wavefront profile and of the starting points is carried out for further treatment subareas a at different points in time, for example, periodically according to a prescribed time schedule, after the breakdown of the eye tissue in all the planned treatment subareas a on a treatment surface w, $w_1$, $w_2$ after the treatment of all the planned treatment subareas a and/or after the reception of an instruction signal input via a user interface.

In a further embodiment, the opthalmological apparatus 1 comprises an eye tracking module 12 (a so-called eye tracker) for determining eye movements. The eye tracking module 12 comprises, for example, a camera, for example, a CCD (Charged Coupled Device) camera, and an illumination device (for example, LEDs) for acquiring a top view of the eye 2, as well as processing means for determining the iris or vein pattern (on the sclera or the retina) in top view, and for determining eye movements on the basis of relative displacements of the iris or vein pattern. The processing means are designed as a programmed logic module by means of software and/or hardware and are arranged in the control module 13 in one variant. Detected eye movements are transmitted continuously from the eye tracking module 12 to the positioning module 16 or to the control module 13, for example, as relative values in relation to a defined reference position for the eye 2, or as values of the direction of view of the eye 2. The positioning module 16 or the control module 13 is configured to compensate movements of the eye 2 during the positioning of the focal point F at a starting point, doing so on the basis of the eye movements determined. The positioning module 16 corrects the coordinates of prescribed starting points on the basis of the detected eye movements, or the control module 13 supplies the positioning module 16 with starting points whose coordinates are adapted in accordance with the eye movements.

The control module 13 is preferably designed as a programmed logic module by means of software and/or hardware. The control module 13 is connected to the positioning module 16 and the scanning module 15 in order to transmit control signals and/or control data. Depending on embodiment, the control module 13 is connected to the wavefront detector 18 and/or the eye tracking module 12 in order to receive feedback or data values created by eye movements. The control module 13 is arranged in a separate housing or in a common housing with the light projection module 11. In the interests of a desired refractive correction of the eye 2, in particular the cornea 21, the control module 13 is configured to determine the spatial distribution of the treatment subareas a required therefore in the interior of the eye 2, that is to say the number of the treatment subareas a, the respectively assigned starting points (in a number of treatment surfaces) and, in one variant, also the corresponding scanning pattern p or the size, shape and/or alignment of the treatment subareas a defined by the scanning pattern p. In one variant, the control module 13 is configured to determine the wavefront profile of a light bundle reflected by the eye 2, and thus the current refractive power of the cornea 21 by means of the wavefront detector 18, and, on the basis thereof, the spatial distribution of the treatment subareas a in the interior of the eye 2.

The control module 13 determines the number and spatial distribution of the treatment subareas a for example on the basis of a table. The table respectively assigns a number and spatial distribution of the treatment subareas a to different refractive correction values (and types of correction). In a further variant, the control module 13 determines the number and spatial distribution of the treatment subareas a on the basis of a model of the eye tissue to be treated, for example, a corneal model, and information on how the eye 2 images for a given size and shape of the treatment subareas a and prescribed vertical and horizontal minimum spacings of individual treatment subareas a. The data on the number and spatial distribution of the treatment subareas a can also be transmitted to the control module 13 by an external unit. The spatial distribution of the treatment subareas a is performed such that the cavities produced upon the breaking down of the eye tissue in the treatment subareas a are respectively separated from one another by tissue bridges both on the same treatment surface w, $w_1$, $w_2$ and in neighboring, superimposed treatment surfaces $w_1$, $w_2$. In one variant, the number of the treatment subareas a can also be determined from an ablation volume which is determined for a specified refractive correction or input by the user. The spatial arrangement of the treatment subareas a is determined by the type of correction, for example the cornea 21 must be flattened off by centralized ablation in the case of a myopia, whereas in the case of a hyperopia it is necessary to configure a steeper curvature of the corneal surface by annularly circulating ablation.

Figure 2:
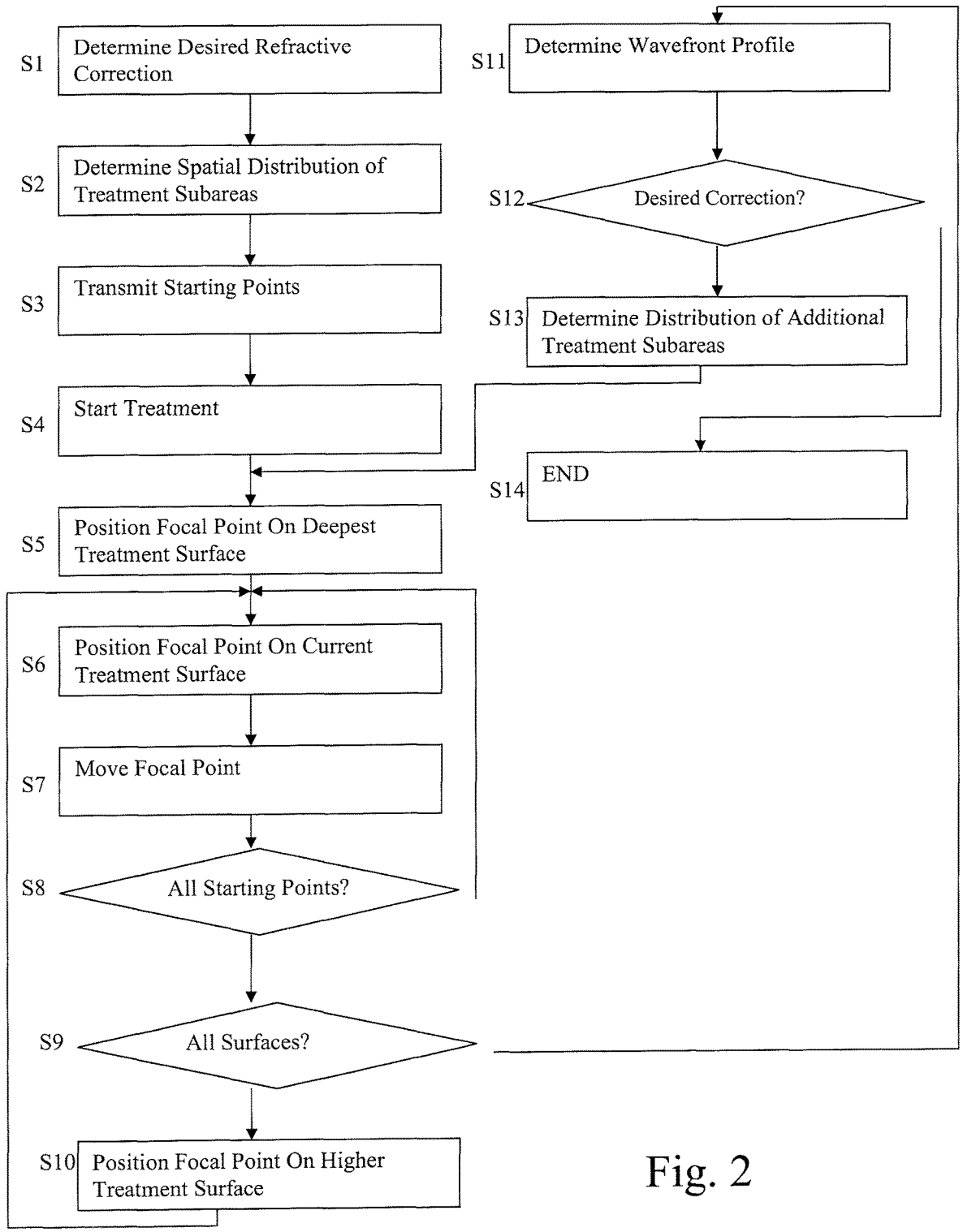
FIG. 2 shows a flowchart which illustrates the cycle in the refractive correction of eye tissue by the breakdown of tissue in a multiplicity of mutually separated treatment subareas.

The following paragraphs describe the cycle, controlled by the control module 13, in the refractive correction of an eye 2 with reference to FIG. 2.

In step S1, the control module 13 determines the desired refractive correction of the eye 2. The desired value of the refractive correction is, for example, input via a user interface and is recorded in the control module 13.

In step S2, the control module 13 determines the spatial distribution of the treatment subareas a in order to achieve the desired refractive correction.

In the optional step S3, the control module 13 transmits the starting points for the scanning pattern p of the treatment subareas a to the positioning module 16, for example, as a sequence of starting points, ordered in terms of decreasing depths of the treatment surface w, $w_1$, $w_2$. In one variant, the various starting points are also assigned identification elements of different scanning patterns p. If appropriate, control values for different scanning patterns p are also transmitted to the scanning module 15.

In step S4, the treatment of the eye 2 is started by a starting signal input via the user interface.

In step S5, the focal point F is positioned on the deepest lying treatment surface $w_1$. The depth positioning module 14 is driven correspondingly, preferably by the control module 13.

In step S6, the positioning module 16 positions the focal point F on the current treatment surface w, $w_1$, $w_2$ at a starting point not yet used. The positioning is performed in accordance with the stipulation of the starting point by the control module 13 or in accordance with a sequence of starting points which has previously been stored in the positioning module 16. The permanently tracked eye movements are also taken into account during the positioning and compensated either in the control module 13 or in the positioning module 16.

In step S7, the scanning module 15 moves the focal point F on the current treatment surface w, $w_1$, $w_2$, starting from the current starting point in accordance with the scanning pattern p which is assigned to the current starting point. The scanning pattern p to be used is, for example, unchanged for the entire treatment, or is determined by the control module 13 or the positioning module 16, for example during the transmission of a synchronization signal, by means of an identification element.

In step S8, the control module 13 checks whether all the starting points of the current treatment surface w, $w_1$, $w_2$ have already been treated. If starting points to be processed remain, the positioning of the next starting point is performed in step S6. The control module continues in step S9 if all the assigned starting points have been processed on the current treatment surface w, $w_1$, $w_2$.

In step S9, the control module 13 checks whether all the treatment surfaces w, $w_1$, $w_2$ have already been treated. If treatment surfaces w, $w_1$, $w_2$ to be treated remain, the focal point F is positioned in step S10 on the equidistant (for example parallel) treatment surface $w_1$, $w_2$ lying higher, on which starting points are to be processed, and the positioning module 16 continues in step S6 with the positioning of the next starting point. Otherwise, the control module continues in step S11 when all the treatment surfaces w, $w_1$, $w_2$ with output points to be processed have already been treated.

In the optional step S11, the wavefront detector 18 determines the wavefront profile of the eye 2 and transmits the latter to the control module 13 (without steps S11, S12, S13 the method ends in step 14).

In step S12 the control module 13 determines on the basis of the wavefront profile whether the desired refractive correction has been achieved. If the desired correction has been achieved, the control module 13 terminates the method in step S14 for example, with the aid of a success message via the user interface. Otherwise, when the desired refractive correction has not yet been achieved the control module continues in step S13.

In step S13, the control module 13 determines, preferably after feedback has been given and confirmation via the user interface, the spatial distribution of additional treatment subareas a which are to be treated in order to achieve the desired refractive correction. The treatment of the further subareas a is performed in step S5, if appropriate after the transmission of the additional starting points to the positioning module 16.

The invention claimed is:

1. An ophthalmological apparatus for a refractive correction of a human eye, comprising:
   a light projector configured to project laser pulses on to a focal point in the interior of the eye for breaking down eye tissue;
   a scanning system with a cascaded first scanner and second scanner,
   the first scanner being configured to position the focal point at different starting points in the interior of the eye, each starting point corresponding to a starting point of a treatment subarea and
   the second scanner being configured to scan the treatment subarea in the interior of the eye with a number of laser pulses by moving the focal point,
   starting from the starting point of the treatment subarea and
   moving the focal point in accordance with a scanning pattern; and
   a control module, connected to the scanner system and configured to control the first scanner to position the focal point at a plurality of starting points in the interior of the eye, using data with the plurality of starting points for a spatial distribution of a plurality of treatment subareas used for the refractive correction of the human eye,
   whereby the plurality of treatment subareas are mutually separated from each other and arranged on greater than three superimposed treatment surfaces inside the eye tissue,
   starting in the spatial distribution on a deepest lying treatment surface in the eye and
   moving on to a neighboring, superimposed treatment surface in the spatial distribution, once all of the plurality of treatment areas have been processed on a respective treatment surface in the spatial distribution,
   until all treatment areas have been processed on all of the greater than three treatment surfaces in the spatial distribution, and
   to control the second scanner to scan each one of the plurality of treatment subareas from its respective starting point,
   breaking down the eye tissue to form a plurality of cavities on greater than three superimposed treatment surfaces inside the eye tissue,
   each cavity being formed by a number of laser pulses moved by the second scanner in accordance with the scanning pattern,
   each cavity corresponding to one of the plurality of treatment subareas
   such that the respective cavity is fully enclosed by tissue and
   separated and disconnected by tissue bridges from other cavities arranged on the same treatment surface and on neighboring, superimposed treatment surfaces, and
   each cavity having no tissue bridges therein.

2. The apparatus according to claim 1, wherein the first scanner is configured to position the focal point at starting points on a first treatment surface, the second scanner is configured to move the focal point on the first treatment surface, and the first scanner comprises a movable focusing lens configured to displace the focal point along a projection axis of the light projector on to a second treatment surface equidistant from the first treatment surface such that the focal point can be positioned on the second treatment surface at different starting points and can be moved in accordance with the scanning pattern starting from one of the starting points.

3. The apparatus according to claim 2, wherein the control module is further configured to control the movable focusing lens such that a minimum distance between the treatment surfaces is observed upon displacement of the focal point, the minimum distance being defined such that treatment subareas superimposed on equidistant treatment surfaces are separated from one another by tissue bridges.

4. The apparatus according to claim 1, wherein the apparatus further comprises a wavefront detector configured to determine a wavefront profile of a light bundle reflected by the eye, and the control module is further configured to define the starting points on the basis of the determined wavefront profile.

5. The apparatus according to claim 1, wherein the second scanner is configured to position consecutive laser pulses such that their focal diameters partially overlap.

6. The apparatus according to claim 5, wherein the focal diameters of the consecutive laser pulses overlap at least as far as half the diameter of the consecutive laser pulses.

7. The apparatus according to claim 1, wherein the scanning pattern defines a treatment subarea whose shape is selected as one of rectangular, round, elliptical, that of a star, that of a spiral and that of a Lissajou figure.

8. The apparatus according to claim 1, wherein the first scanner is configured to position the focal point at starting points in the cornea of the eye.

9. The apparatus according to claim 1, wherein, for deflecting the laser pulses, the second scanner comprises at least one of the following: a galvanoscanner, a resonant mirror scanner, an acoustic optical modulator, a polygonal scanner and a microelectromechanical scanner.

10. The apparatus according to claim 1, wherein the first scanner comprises movement drivers for mechanically displacing at least parts of the light projector.

11. The apparatus according to claim 1, wherein the first scanner comprises a galvanoscanner for deflecting the laser pulses.

12. The apparatus according to claim 1, wherein the light projector has a numerical aperture above 0.3.

13. The apparatus according to claim 1, wherein the plurality of mutually separated treatment subareas include one hundred or more mutually separated treatment subareas.

14. The apparatus according to claim 1, wherein the control module is configured to determine the data with the plurality of starting points for the spatial distribution of the plurality of treatment subareas from a table.

15. The apparatus according to claim 1, wherein the control module is configured to receive the data with the plurality of starting points for the spatial distribution of the plurality of treatment subareas from an external entity.

* * * * *